(12) United States Patent
Vaska et al.

(10) Patent No.: US 9,655,768 B2
(45) Date of Patent: May 23, 2017

(54) ORAL DEVICE FOR MANDIBULAR ADVANCEMENT AND MEDIAL TONGUE CONSTRAINT

(71) Applicant: ApniCure, Inc., Redwood, CA (US)

(72) Inventors: Matthias Vaska, Palo Alto, CA (US); Jonathan L. Podmore, San Carlos, CA (US); John Edwards Crowe, Menlo Park, CA (US); Sean Christopher Daniel, Palo Alto, CA (US)

(73) Assignee: ApniCure, Inc., Redwood City, CA (US)

( * ) Notice: Subject to any disclaimer, the term of this patent is extended or adjusted under 35 U.S.C. 154(b) by 0 days.

(21) Appl. No.: 14/978,310

(22) Filed: Dec. 22, 2015

(65) Prior Publication Data

US 2016/0106571 A1    Apr. 21, 2016

Related U.S. Application Data

(60) Continuation-in-part of application No. 13/781,996, filed on Mar. 1, 2013, now Pat. No. 9,241,825, which
(Continued)

(51) Int. Cl.
*A61F 5/56*    (2006.01)
*A61M 16/04*    (2006.01)

(52) U.S. Cl.
CPC ......... *A61F 5/566* (2013.01); *A61M 16/0463* (2013.01); *A61M 16/0488* (2013.01)

(58) Field of Classification Search
CPC ...... A61F 5/566; A61F 5/56; A61F 2005/563; A61F 2/20; A61F 2/00; A61B 17/663;
(Continued)

(56) References Cited

U.S. PATENT DOCUMENTS

| 4,898,535 A | 2/1990 | Bergersen |
| 5,957,133 A * | 9/1999 | Hart ........................ A61F 5/566 128/200.26 |

(Continued)

FOREIGN PATENT DOCUMENTS

| EP | 2269543 A1 | 1/2011 |
| WO | WO-2011126854 A2 | 10/2011 |

OTHER PUBLICATIONS

International search report and written opinion dated Jun. 3, 2014 for PCT/US2014/0180149.
(Continued)

*Primary Examiner* — Ophelia A Hawthorne
(74) *Attorney, Agent, or Firm* — Wilson, Sonsini, Goodrich & Rosati

(57) ABSTRACT

An oral device for temporary placement in a patient's oral cavity includes upper and lower jaw braces and a tongue-engaging member. The upper and lower jaw braces are connected so that the lower jaw brace is advanced in an anterior direction relative to the upper jaw brace when the upper and lower jaw braces are closed together. A partial vacuum is drawn in the oral cavity and the vacuum and lower jaw displacement together control the position of the tongue in order to clear the patient's airway to reduce sleep apnea or treat other conditions.

25 Claims, 7 Drawing Sheets

Related U.S. Application Data is a continuation-in-part of application No. 13/365,791, filed on Feb. 3, 2012, now Pat. No. 8,656,922, which is a division of application No. 12/269,683, filed on Nov. 12, 2008, now Pat. No. 8,122,889.

(60) Provisional application No. 60/987,707, filed on Nov. 13, 2007.

(58) Field of Classification Search
CPC ........... A61C 8/0096; A61C 7/10; A61C 7/00; A61C 7/08; A61C 2201/007; A63B 2071/088; A63B 2208/12; A63B 71/085; A61M 16/0463; A61M 16/0488
See application file for complete search history.

(56) References Cited

U.S. PATENT DOCUMENTS

| | | | |
|---|---|---|---|
| 6,467,484 B1 | 10/2002 | De Voss | |
| 6,526,982 B1 | 3/2003 | Strong | |
| 6,997,177 B2* | 2/2006 | Wood | A61M 16/0666 |
| | | | 128/200.24 |
| 7,328,698 B2* | 2/2008 | Scarberry | A61F 5/566 |
| | | | 128/200.24 |
| 7,770,582 B2* | 8/2010 | Chen | A61F 5/566 |
| | | | 128/848 |
| 7,861,721 B2* | 1/2011 | Bergersen | A61F 5/566 |
| | | | 128/848 |
| 8,074,656 B2 | 12/2011 | Vaska et al. | |
| 8,122,889 B2 | 2/2012 | Vaska et al. | |
| 8,122,890 B2 | 2/2012 | Vaska | |
| 8,387,620 B1* | 3/2013 | Vaska | A61F 5/566 |
| | | | 128/848 |
| 8,505,540 B2 | 8/2013 | Vaska et al. | |
| 8,573,223 B2* | 11/2013 | Podmore | A61F 5/566 |
| | | | 128/848 |
| 8,656,922 B2 | 2/2014 | Vaska et al. | |
| 9,241,825 B2* | 1/2016 | Vaska | A61F 5/566 |
| 2005/0028826 A1 | 2/2005 | Palmisano | |
| 2005/0166928 A1* | 8/2005 | Jiang | A61F 5/566 |
| | | | 128/861 |
| 2007/0074729 A1 | 4/2007 | Magnin | |
| 2007/0292819 A1 | 12/2007 | Scarberry et al. | |
| 2009/0120446 A1 | 5/2009 | Vaska et al. | |
| 2010/0043805 A1 | 2/2010 | Kelly | |
| 2011/0000495 A1 | 1/2011 | Ash | |
| 2012/0017917 A1 | 1/2012 | Podmore et al. | |
| 2012/0024297 A1 | 2/2012 | Hegde et al. | |
| 2012/0103345 A1 | 5/2012 | Gay | |
| 2012/0145166 A1 | 6/2012 | Fallon et al. | |
| 2013/0186411 A1 | 7/2013 | Vaska et al. | |
| 2013/0263866 A1 | 10/2013 | Vaska et al. | |
| 2015/0157492 A1 | 6/2015 | Vaska et al. | |

OTHER PUBLICATIONS

Notice of allowance dated Sep. 17, 2015 for U.S. Appl. No. 13/781,996.
Office action dated Jun. 16, 2015 for U.S. Appl. No. 13/781,996.
Office action dated Dec. 18, 2014 for U.S. Appl. No. 13/781,996.
European search report and search opinion dated Oct. 27, 2016 for EP Application No. 14756723.4.

\* cited by examiner

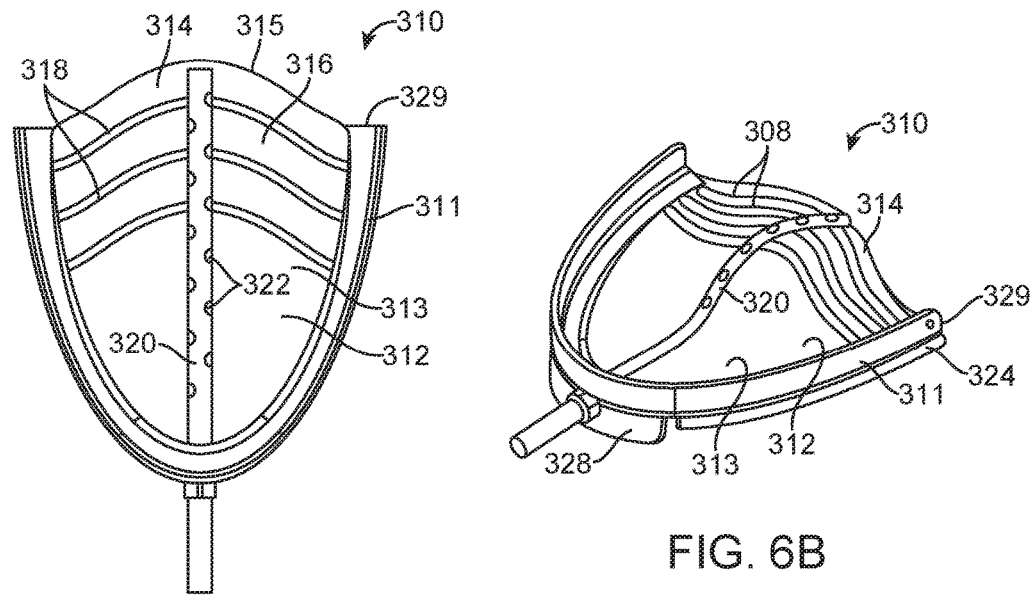
FIG. 6A
FIG. 6B
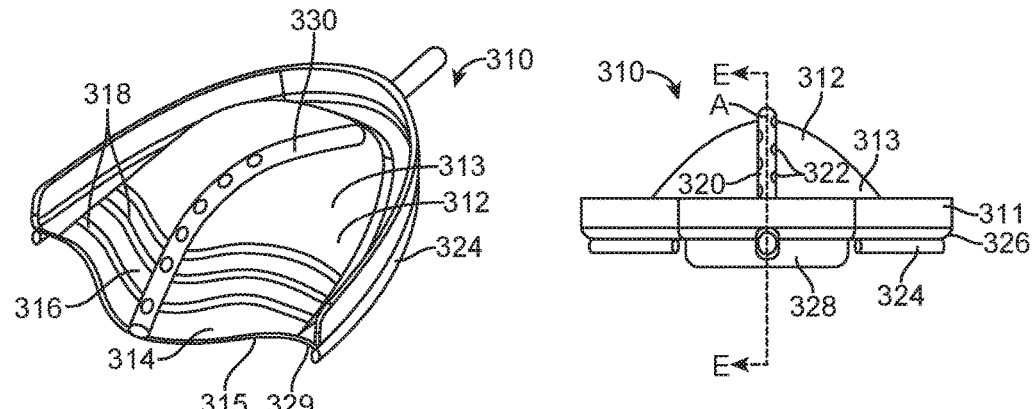
FIG. 6C
FIG. 6D
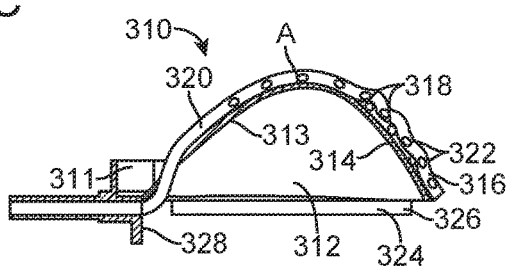
FIG. 6E

ORAL DEVICE FOR MANDIBULAR ADVANCEMENT AND MEDIAL TONGUE CONSTRAINT

CROSS-REFERENCE TO RELATED APPLICATIONS

The present is a continuation-in-part of U.S. patent application Ser. No. 13/781,996, filed on Mar. 1, 2013, now U.S. Pat. No. 9,241,825, which is a continuation-in-part of U.S. patent application Ser. No. 13/365,791, filed on Feb. 3, 2012, now U.S. Pat. No. 8,656,922, which is a divisional of U.S. patent application Ser. No. 12/269,683, filed Nov. 12, 2008, now U.S. Pat. No. 8,122,889, which claims the benefit of provisional U.S. application Ser. No. 60/987,707, filed Nov. 13, 2007, the full disclosures of which are incorporated herein by reference.

This application is also a continuation-in-part of U.S. patent application Ser. No. 14/626,097, filed on Feb. 19, 2015, which is a continuation of U.S. patent application Ser. No. 13/912,021, filed Jun. 6, 2013, which is a continuation of U.S. patent application Ser. No. 12/882,054, filed on Sep. 14, 2010, now U.S. Pat. No. 8,505,540, which is a continuation-in-part of U.S. patent application Ser. No. 12/269,683, filed on Nov. 12, 2008, now U.S. Pat. No. 8,122,889, which claims the benefit of U.S. Provisional Application No. 60/987,707, filed Nov. 13, 2007, the full disclosures of which are incorporated herein by reference; U.S. patent application Ser. No. 12/882,054, filed on Sep. 14, 2010, is also a continuation-in-part of U.S. patent application Ser. No. 12/840,076, filed on Jul. 20, 2010, the full disclosures of which are incorporated herein by reference.

BACKGROUND OF THE INVENTION

Field of the Invention

The present invention relates generally to medical devices and methods. In particular, the present invention relates to an oral device that may be held in the mouth of a patient to reduce the incidence of obstructive sleep apnea or snoring.

Obstructive sleep apnea (OSA) is a serious medical condition resulting from a temporary airway blockage which occurs as a patient sleeps. The airway blockage usually occurs between the soft palate and/or the back of the tongue and the pharynx. As the patient breathes, the reduced area in the upper airway can cause snoring, and more seriously, OSA. Sleep disruption caused by OSA can result in severe daytime sleepiness, chronic fatigue, headaches, depression, accidents, injuries, and of particular concern, OSA can reduce the amount of oxygen entering the lungs causing hypoxia. Hypoxia, in turn, can lead to pulmonary hypertension, heart disease, and stroke.

Numerous invasive and less invasive treatments have been proposed for OSA. Of particular interest to the present invention, "continuous positive airway pressure" (CPAP) delivers a continuous stream of pressurized air directly to the person's upper airway. The positive pressure maintains patency of the airway and inhibits the airway collapse associated with OSA. Although generally effective, CPAP suffers from a number of drawbacks that have led to a high level of non-compliance. The patient must wear a bulky facial mask which can be uncomfortable, and the system generates noise that can make falling asleep difficult. CPAP is also difficult to use because the mask requires careful fitting to avoid air leaks and facial discomfort and because the mask can easily be dislodged during sleep. Moreover, a number of unpleasant side effects, such as sore throats, dry throat and eyes, headaches, and skin rashes from the mask frequently occur. These problems have resulted in a high level of non-compliance with CPAP therapy.

As an alternative to CPAP, the use of mandibular advancement devices, often referred to as a mandibular splint or a mandibular advancement splint, has been proposed. A mandibular advancement device is an oral appliance worn in the mouth over the upper and lower teeth. The device treats snoring and sleep apnea by moving the lower jaw forward slightly, which tightens the soft tissue and muscles of the upper airway to inhibit obstruction of the airway during sleep. The tightening created by the device may also suppress vibrating of the soft tissues of the upper airway as air passes over them, which is the most common cause of loud snoring. While often effective, such mandibular advancement devices can cause significant jaw discomfort and can cause teeth to shift over time, leading to significant dental problems.

A recent significant improvement in the treatment of sleep apnea is described in U.S. Pat. Nos. 8,074,656; 8,074,656; and 8,122,889, U.S. Patent Publication 2012/0017917, and copending application Ser. No. 13/593,137, each assigned to the assignee of the present application, the full disclosures of which are incorporated herein by reference. These patents and applications describe engaging a lateral element across a medial region of the tongue to create a clearance above the tongue. By drawing a vacuum in the oral cavity, the soft palate can be drawn forward to open the airway. While very successful in many patients, the treatment is not fully effective in some patients.

For these reasons, it would be desirable to provide alternative and improved methods and apparatus for treating obstructive sleep apnea and snoring. The methods and devices should be non-invasive and require no surgery or permanently implanted components. In addition, the methods and devices should be minimally intrusive with components that are comfortable and quiet so that disruption of the patient's sleep is minimized. The methods and devices should reduce any risk of tooth displacement associated with mandibular advancement or other causes. Moreover, the methods and devices should avoid contacting the portions of the oral cavity that trigger the gag reflex. The methods and systems should also be simple to implement and be effective to significantly improve patency of a patient's airway during sleep in a broad population of patients suffering from sleep apnea. At least some of these objectives will be met by the inventions described hereinafter.

Description of the Background Art

U.S. Pat. Nos. 8,074,656; 8,122,889; and 8,122,890; U.S. Patent Publication No. 2012/007917; and co-pending application Ser. No. 13/593,137, each assigned to the assignee of the present application, are described above. U.S. Patent Publication Nos. 2005/0028826; 2007/0074729; 2010/0043805; and 2011/000495, the full disclosures of which are incorporated herein by reference, describe various mandibular advancement devices.

SUMMARY OF THE INVENTION

The present invention provides methods and devices for maintaining patency (openness) in a patient's airway by simultaneously advancing the patient's lower jaw and depressing a medial region of the patient's tongue while applying a vacuum in the oral cavity. Advancing the lower jaw, referred to as mandibular advancement, draws the tongue forward while applying the vacuum simultaneously draws the soft palate forward. Together these movements clear the airway more reliably and for a greater number of patients than either action can consistently achieve by itself. Moreover, by applying the two actions together, the degree to which either action must be performed can be reduced. In particular, for patients sensitive to lower jaw advancement, the degree to which the jaw must be advanced can be reduced with the application of pressure restoring any therapeutic benefit that might otherwise be lost. Alternatively, for patients sensitive to the applied vacuum, the level of vacuum can be reduced while relying on jaw advancement to make up for any lost therapeutic benefit. In other cases, of course, both the jaw advancement and the pressure therapy can be applied at or near their full therapeutic levels in order to provide a therapeutic benefit which can be greater than either can achieve by itself.

In a first aspect of the present invention, an oral device for temporary placement in a patient's oral cavity comprises an upper jaw brace and a lower jaw brace. A tongue-engaging member is coupled to at least one of the upper and lower jaw braces, usually to the upper jaw brace, and is disposed to engage a medial region of the tongue when the upper jaw brace is positioned on the upper jaw. The upper and lower jaw braces are connected so that the lower jaw brace is advanced in an anterior direction relative to the upper jaw brace when the upper and lower jaw braces are closed together.

The upper and lower jaw braces may take a variety of forms. While the exemplary jaw braces will usually comprise a U-shaped bite plate configured to be positioned over the patient's full dentition (all teeth in the upper or lower jaw), the braces could be any assembly or structure which can be removably attached to the patient's upper or lower teeth or jaw with sufficient purchase so that manipulating the relative positions of the upper and lower jaw braces can advance the lower jaw by a desired distance, typically at least 4 mm, usually in the range from 4 mm to 12 mm, and typically in the range from 5 mm to 10 mm. Other exemplary jaw braces include tooth retainer structures formed to have a negative cavity fitting precisely over the teeth, typically by vacuum molding from plaster or other cast of the teeth. Other jaw braces of a type used in mandibular advancement devices can also be used. For example, such devices can be formed from ethylene vinyl alcohols (EVA's) which can be heated for softening and then molded to a patient's dentition.

The upper and lower jaw braces may be attached to each other in a variety of ways. Most simply, the upper and lower jaw braces can be permanently affixed to each other with the lower jaw brace advanced by a fixed distance relative to the upper jaw brace. Frequently, however, it is desirable to provide adjustability, which can be achieved using, for example, a "Herbst-style" device having two rigid links on the outside of the braces. The links can have an adjustable length. Moreover, by pivotally attaching the links to both braces, the patient can also have some freedom to open and close his or her jaws. In other cases, the upper and lower braces can be attached using elastic bands attached to anchors on the braces where the bands and anchors are arranged to pull the lower jaw forward.

In these specific embodiments, a vacuum source is connectable to the oral device, typically via the tongue-engaging member. The vacuum source is adapted to draw a vacuum in the range from 1 cm $H_2O$ to 100 cm $H_2O$, preferably from 25 cm $H_2O$ to 50 cm $H_2O$. The tongue-engaging member will typically have a vacuum port and a bleed port which connect to the vacuum source in order to provide a continuous airflow through the tongue-engaging member while maintaining a partial vacuum in the oral cavity. In the specific embodiments, the tongue-engaging member has an anterior surface and a posterior surface where the anterior surface is inclined forwardly relative to a plane of the patient's jaw and is disposed to engage a medial region of the tongue when the upper jaw brace is on the upper jaw. Usually, the tongue-engaging member has an integral plenum connectable to the vacuum source and has at least one port disposed on a posterior surface which is open to the integral plenum. Typically, the tongue-engaging member will have a plurality of ports distributed over the posterior surface. The anterior and posterior surfaces of the tongue-engaging member are usually inclined forwardly at an angle in the range from 45° to 60° relative to a plane of the upper jaw brace when positioned on the upper jaw. The anterior surface of the tongue-engaging member will usually be generally parallel to the posterior surface.

In a second aspect of the present invention, a method for stabilizing a soft palate in a patient's oral cavity comprises engaging a member against a medial region of the patient's tongue to provide a clearance between the medial region and the patient's-palate. A vacuum is applied within the clearance to draw together the soft palate and the posterior region of the tongue, and a lower jaw of the patient is advanced forwardly relative to an upper jaw while applying the vacuum. By simultaneously drawing the lower jaw forward (mandibular advancement) and applying a vacuum to draw the soft palate forward (oral pressure therapy), improved therapies to a potentially greater number of patients are provided. In particular, the degree to which either the mandibular advancement or the oral pressure therapy need be applied can be reduced, or by applying both the mandibular advancement and the oral pressure therapy at their full therapeutic levels, the effectiveness of the combined therapies can be increased relative to either therapy alone.

Advancing the lower jaw relative to the upper jaw typically comprises capturing the upper jaw in an upper jaw brace and capturing the lower jaw in a lower jaw brace. The braces are connected so that the lower jaw brace moves in an anterior direction relative to the upper jaw brace when the jaws are closed together. Such therapy typically advances the lower jaw relative to the upper jaw by distance and range from 4 mm to 12 mm, usually from 5 mm to 10 mm.

The specific means for attaching the upper and lower jaw braces together have been described above. Similarly, the specific techniques for applying vacuum in the patient's oral cavity have also been described above.

BRIEF DESCRIPTION OF THE DRAWINGS

FIGS. 6A-6E are top, oblique, front and side cross-sectional views, respectively of an oral device according to the invention in a further embodiment thereof, in which the lip seal is removed for clarity.

DETAILED DESCRIPTION OF THE INVENTION

Figure 1:
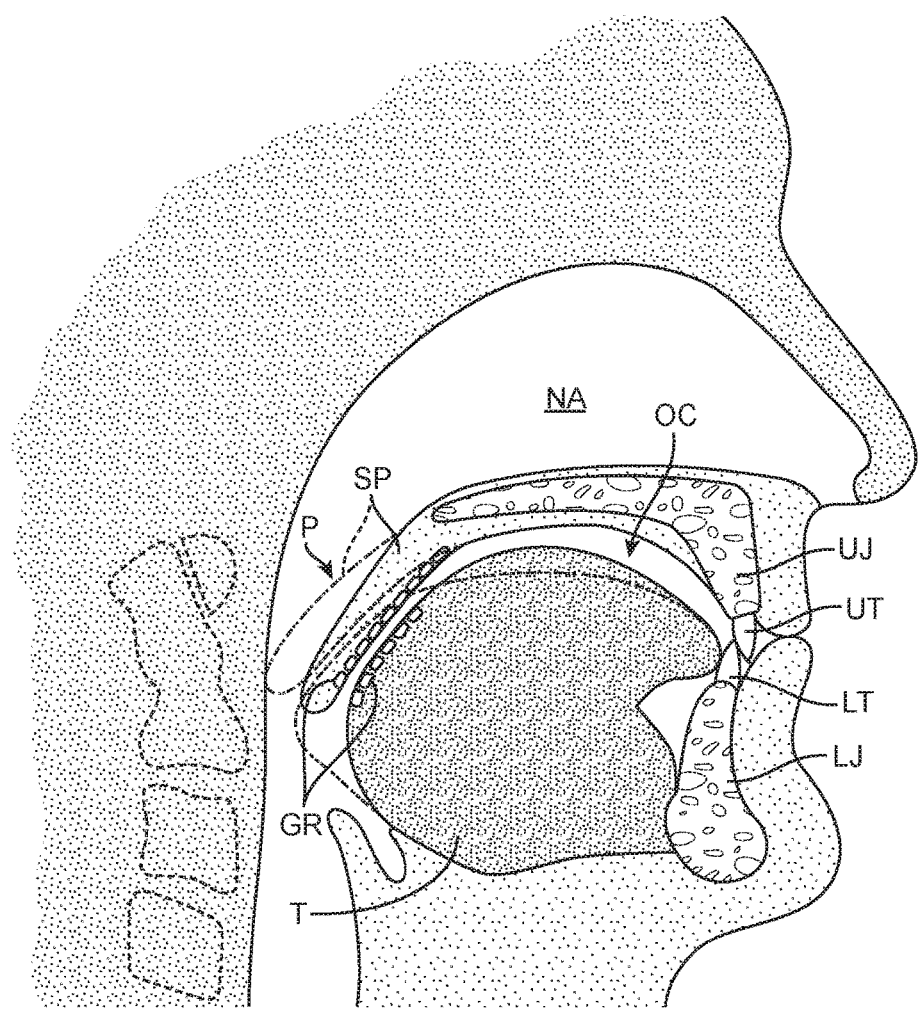
FIG. 1 illustrates the relevant anatomy of the nasal and oral cavities.

Referring to FIG. 1, the anatomy of the oral and nasal cavities relevant to obstructive sleep apnea (OSA) and the placement of the devices of the present invention will be described. The upper teeth UT of the patient are anchored in the hard palate HP, and the lower teeth LT are anchored in the lower jaw or mandible LJ. The soft palate SP extends in a rearward or posterior and inferior direction from the hard palate, and together the hard palate and soft palate divide the nasal airway NA from the oral cavity OC. The lower extent of the oral cavity is largely defined by the upper surface of the tongue T in this view, and it will be appreciated that both the soft palate SP and the tongue are mobile structures capable of movement between the positions shown in full line and broken line in FIG. 1. A nasal airway NA extends inferiorly into the pharynx P which defines the airway generally behind the soft palate SP and the tongue T. The regions on the tongue and soft palate shown with a heavy dashed line are the areas responsible for the gag reflex GR.

Obstructive sleep apnea occurs when the soft palate, the tongue or both move in a posterior direction so that they contact the rear or posterior surface of the pharynx P. The posterior motion of the soft palate and/or tongue may also reduce the size of the airway without contacting the pharynx P causing a partial blockage. The temporary blockage of the airway behind the soft palate and tongue will cause the disrupted breathing pattern characteristic of OSA and usually associated with snoring.

As used herein, "superior" refers to the direction toward the top of the oral cavity (or top of the head), "inferior" refers to the direction opposite the superior direction, "anterior" refers to the direction toward the front of the oral cavity or lips, and "posterior" refers to the direction toward the back of the oral cavity and airway, opposite the anterior direction. The terms "patency" and "airway" refer to the opening or clearing of the airway leading from the nasal cavity into the trachea located generally behind the soft palate and the rear of the tongue. To improve airway patency, the airway may be wholly or partially obstructed intermittently or temporarily for some time period over a normal sleep cycle, however, the airway will be open or partially open more than it would in the patient's untreated condition. The "upper portion of the soft palate" refers to the superior portion of the soft palate extending inferiorly from the end which connects to the hard palate to a point about one-third to one-half way toward the free inferior tip of the soft palate. The phrase "medial region" or "medial surface" of the tongue refers to a superior surface of the tongue which is spaced substantially posteriorly from the anterior tip of the patient's tongue and immediately anterior or forward of the region which initiates the gag reflex. While it may vary from patient to patient, the medial region will generally be the middle one third of the upper surface of the tongue which extends between the anterior tip of the tongue and the posterior end of the tongue (the posterior end being the location on the tongue that is furthest posterior in the oral cavity); i.e., the medial surface will usually include an area of the tongue that is at least about one-third of the way, more preferably at least about one-half of the way, from the anterior tip of the tongue to the posterior end of the tongue. Preferably, the medial region will include an area on the tongue posterior to the midpoint between the anterior and posterior ends of the hard palate. The phrase "clear region" refers to the space or volume above and/or posterior of the tongue which will be cleared by the methods and devices of the present invention. The clearing will usually be achieved by engaging a surface which is inclined forwardly relative to a plane of the brace when the brace is positioned between the upper and lower teeth and against the superior surface of the tongue, typically using a member or element which engages the tongue and which is anchored within the oral cavity so as to simultaneously advance the tongue in an anterior direction and depress the tongue in an inferior direction to open or maintain the clear region and allow the negative pressure to draw the soft palate against the tongue. The term "vacuum" and the phrase "negative pressure" each refers to a total or partial vacuum which is maintained in the clear region, typically by controlled aspiration, where the pressure is maintained primarily in the range from 5 cmH$_2$O to 150 cmH$_2$O below the local atmospheric pressure. The "occlusal plane" is the plane in which the upper and lower teeth meet when the patient bites the upper and lower teeth together.

Figure 2:
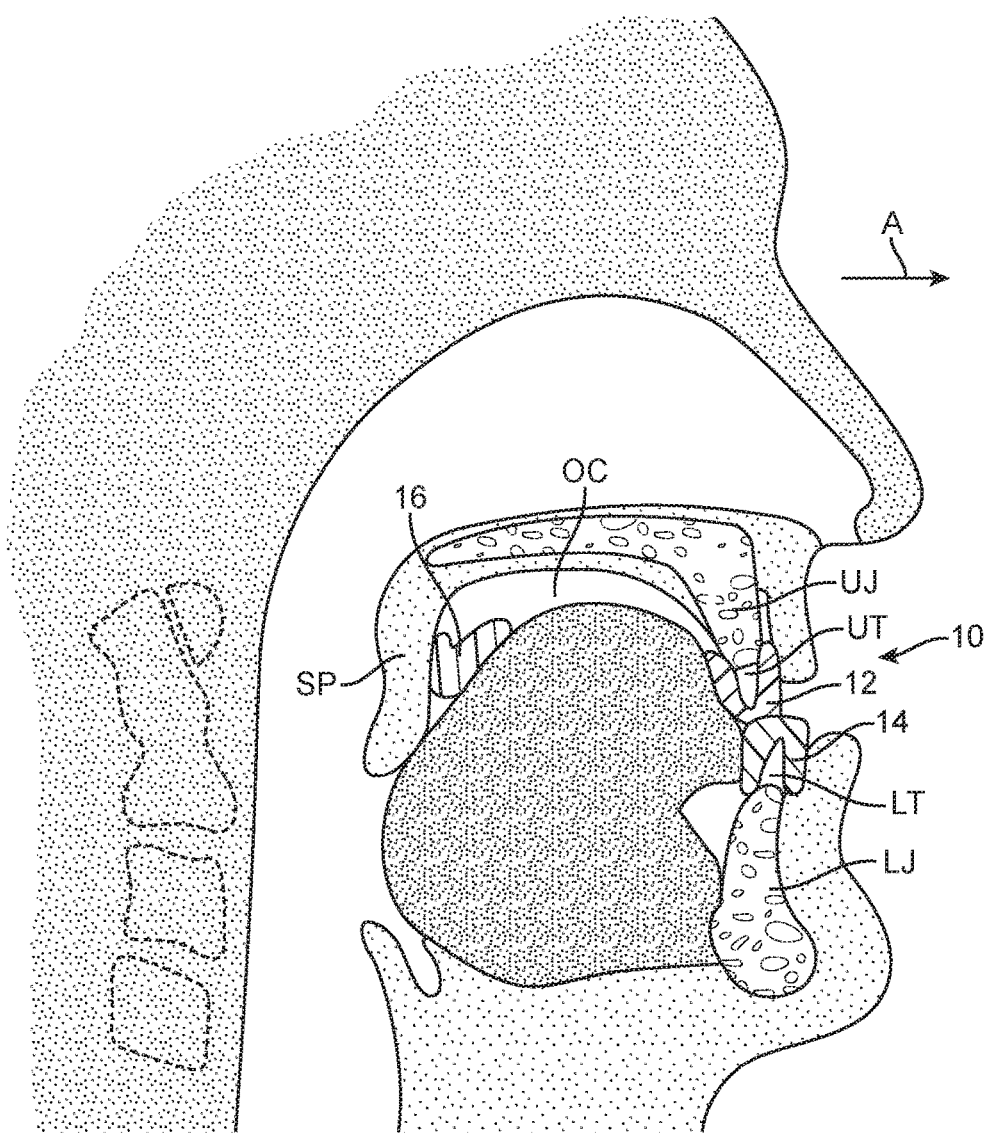
FIG. 2 illustrates the relevant anatomy of the nasal and oral cavities with an oral device of the present invention in place.

Referring now to FIG. 2, use of an oral device 10 comprising an upper jaw brace 12, a lower jaw brace 14, and a tongue-engaging member 16 in performing the methods of the present invention will be described generally. Oral device 10 is placed in the patient's oral cavity OC by the patient. The upper jaw brace 12 is placed over the upper teeth UT and the lower brace is placed over the lower teeth LT. When the patient's jaws are generally closed together, the upper jaw brace 12 and lower jaw brace 14 will be brought together so that occlusal surfaces of the braces will be generally in direct contact with each other, and the tongue-engaging member 16 will be positioned over the medial region of the tongue helping raise the tongue within the oral cavity OC and pushing the tongue forward away from the patient's airway. By simultaneously applying a vacuum in the oral cavity, typically through ports formed on the tongue-engaging member (but optionally formed elsewhere on the oral device 10), the patient's soft palate SP will be drawn forwardly in an anterior direction as indicated by arrow A in FIG. 2, further clearing the patient's airway.

Figure 3A:
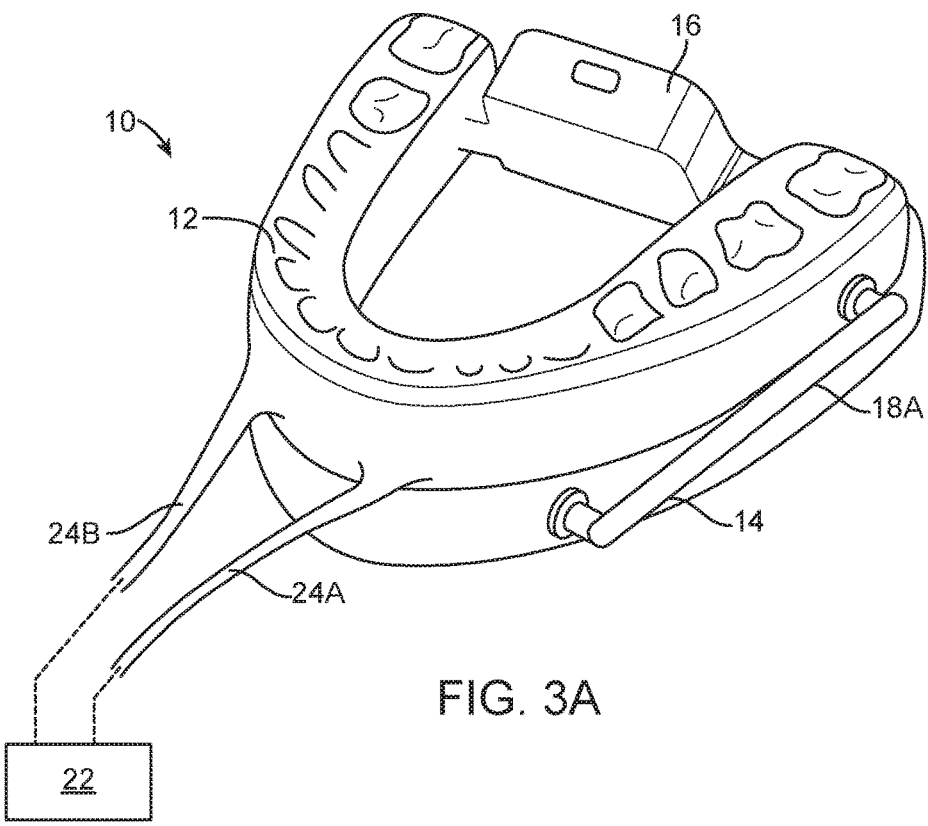
FIGS. 3A and 3B illustrate an embodiment of an oral device constructed in accordance with the principles of the present invention with FIG. 3A providing an anterior to posterior perspective view and FIG. 3B showing an posterior to anterior perspective view.
Figure 3B:
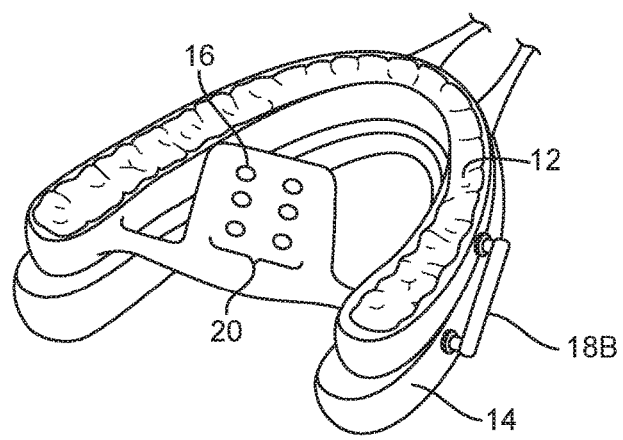
Figure 7A:
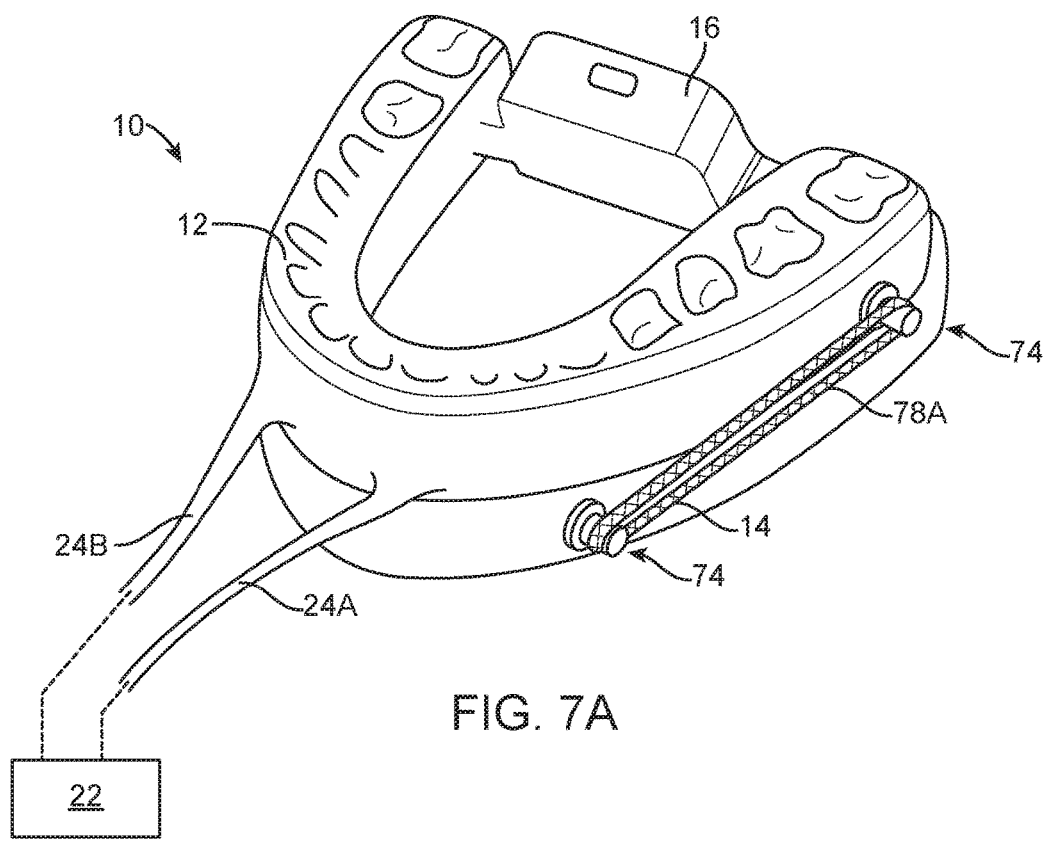
FIGS. 7A and 7B illustrate an embodiment of an oral device constructed in accordance with the principles of the present invention with FIG. 7A providing an anterior to posterior perspective view and FIG. 7B showing a posterior to anterior perspective view.
Figure 7B:
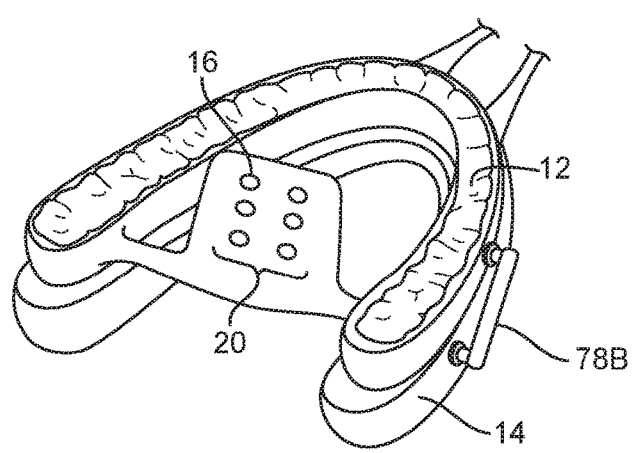

Referring now to FIGS. 3A and 3B, the upper jaw brace 12 and lower jaw brace 14 of the exemplary oral device 10 can be joined together by links 18A and 18B, one on each side of the device. The links may be rigid and fixedly secured to the upper jaw brace 12 and lower jaw brace 14, for example by screws as illustrated in FIGS. 3A and 3B. The lengths of such fixed links can be adjustable, e.g. being formed as a telescoping structure that can be locked in a desired therapeutic position. Additionally, the links 18 may be attached to the upper and lower jaw braces, respectively, by pivoting attachments. When the attachments are pivoting, it will be possible for the patient to at least partially open and close his or her jaws while maintaining the jaw braces on the teeth. Such movement of the jaws, however, will be difficult unless the links 18A and 18B are also capable of elongating to provide the necessary freedom for the jaw to open and close. In cases where the upper and lower jaw braces are fixed, of course, the patient will not be able to open and close his or her jaws while wearing the braces. In other cases, the upper jaw brace 12 and the lower jaw brace 14 can be attached using elastic bands 78A, 78B attached to anchors 74 on the braces 12, 14 as shown in FIGS. 7A and 7B.

The tongue-engaging member 16 will typically have one or more vacuum ports 20 formed on a posterior surface thereof. These vacuum ports 20 are connected to a vacuum source 22 by a pair of vacuum lines 24. A partial vacuum may be maintained within the patient's oral cavity using the vacuum source 22. Usually, a vacuum line 24A while an air bleed is connected to the tongue-engaging member by line 24B. By controlling the vacuum and air bleeds provided through lines 24A and 24B, respectively, the vacuum source can maintain a target vacuum within the oral cavity in the ranges set forth above. Suitable vacuum control systems are described in the commonly owned patents and pending patent application incorporated by reference hereinabove.

Figure 4A:
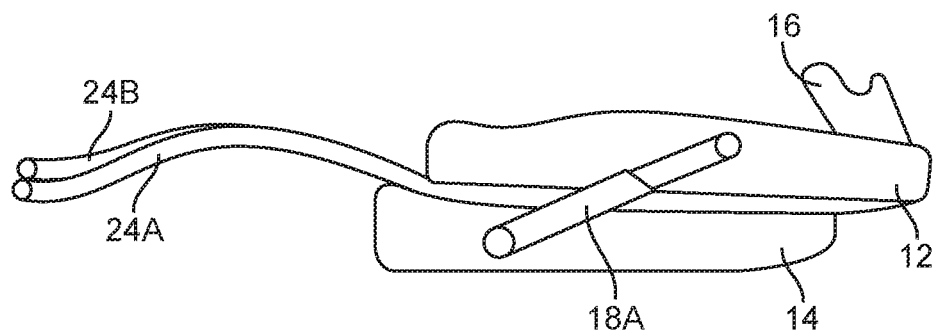
FIGS. 4A and 4B are schematic side views of the oral device of FIGS. 3A and 3B shown with upper and lower jaw braces closed together with the lower brace advanced in an anterior direction relative to the upper brace in FIG. 3A and the with the upper and lower braces opened in FIG. 3B.
Figure 4B:
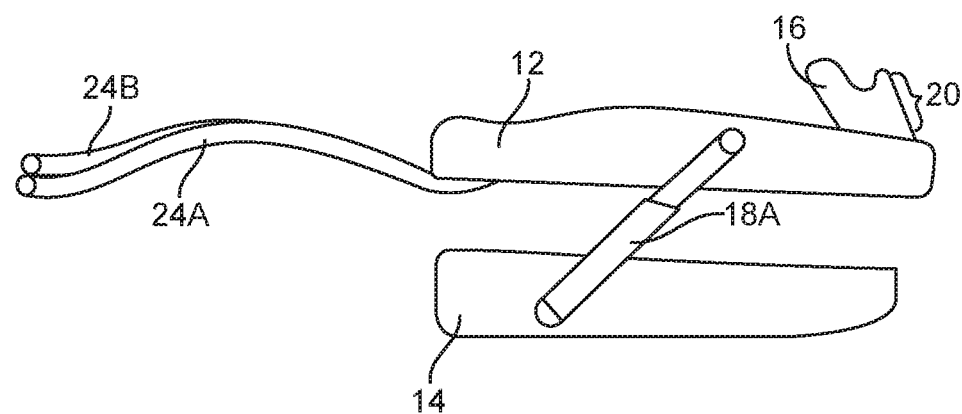
Figure 8A:
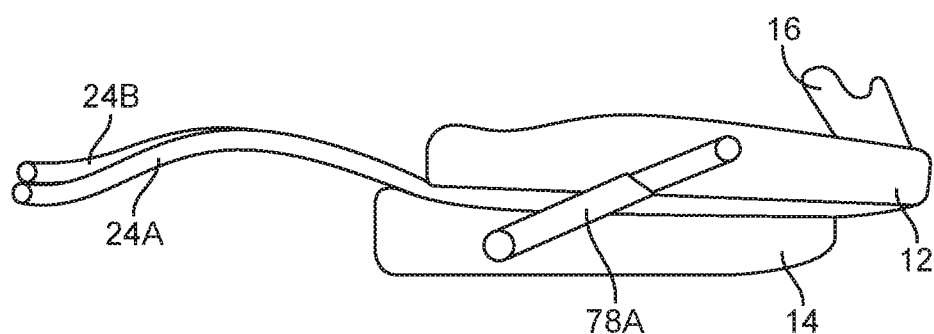
FIGS. 8A and 8B are schematic side views of the oral device of FIGS. 8A and 8B shown with upper and lower jaw braces closed together with the lower brace advanced in an anterior direction relative to the upper brace in FIG. 8A and with the upper and lower braces opened in FIG. 8B.
Figure 8B:
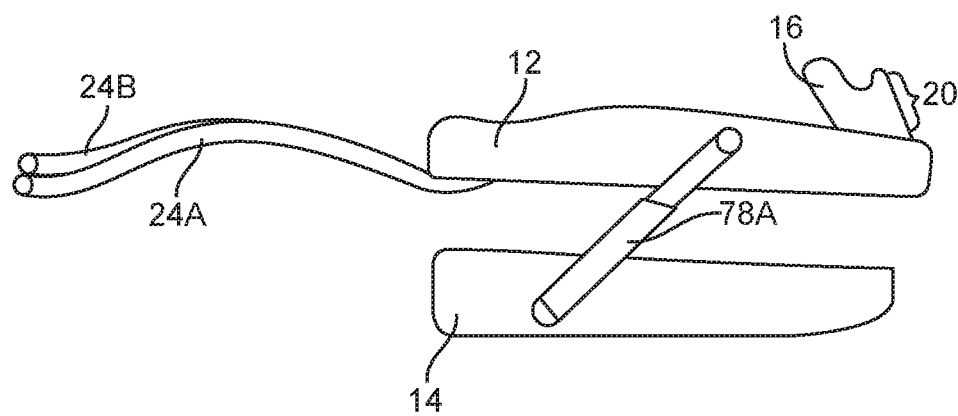

Side views of the oral device 10 are shown in FIGS. 4A and 4B. In 4A, the upper jaw brace 12 is closed downwardly against the lower jaw brace 14 in a configuration in which the device 10 will generally be worn to inhibit snoring and sleep apnea. A particular advantage of the construction of device 10, however, is that should the patient need to open his or her mouth, the links 18A and 18B (only 18A shown in FIGS. 4A and 4B), can pivot and extend to allow the patient to open his or her mouth without dislodging the braces from his or her teeth. When closed, however, the upper brace will again extend anteriorly relative to the lower brace, as shown in FIG. 4A. In other cases, where the upper and lower braces 12, 14 are attached using elastic bands 78A, 78B, the bands 78A, 78B and anchors 74 are arranged to pull the lower jaw forward as shown in FIGS. 8A and 8B.

Figure 5:
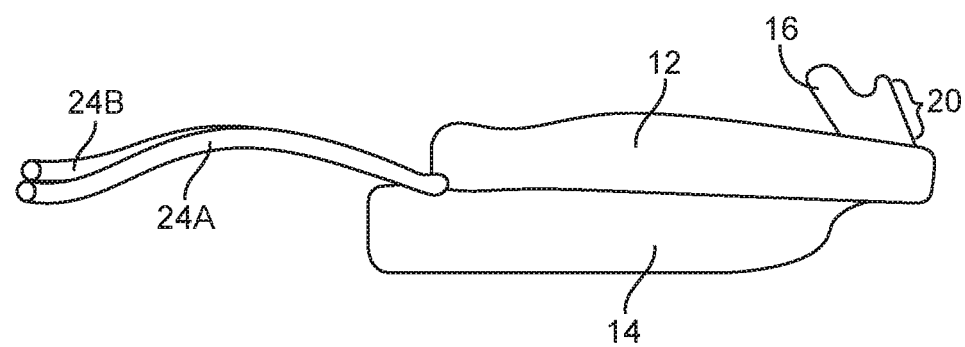
FIG. 5 is a side view of an alternative embodiment of the oral device of the present invention having upper and lower jaw braces permanently affixed to each other.

In an alternative configuration, as shown in FIG. 5, the upper jaw brace 12 and the lower jaw brace 14 may be permanently affixed so that they cannot be opened and closed relative to each other. For example, the components may be molded or formed as an integrated or monolithic structure. Alternatively, the jaw braces may be glued, heat sealed, or otherwise attached together, for example using permanent screws.

Still another embodiment of an oral device according to the invention is illustrated in FIGS. 6A-E. In this embodiment, oral device 310 has a bite structure 311 and a tongue constraint 312 comprising a plate 313 with a soft palate landing pad 314. Landing pad 314 has a posterior edge 315 with an arcuate shape that curves outwardly in the posterior and (optionally) inferior directions beyond the open end of bite structure 311. With this shape landing pad 314 may be more suitably located to engage the soft palate in some patients. In addition, landing pad 314 optionally includes a plurality of ribs 318 extending laterally across landing pad 314. Ribs 318 stand in relief on the posterior surface 316 of landing pad 314 to enhance engagement with the soft palate tissue, as well as help to channel the vacuum flow laterally. Ribs 318 may comprise tubular, round, or partially-round strips affixed to landing pad 314, or ribs 318 may be integrally formed with landing pad 314. Ribs may also be provided along the superior surface of plate 313 oriented either laterally like ribs 318 illustrated, in the anterior-posterior direction, or in other orientations.

The vacuum tube 320 extends past apex A to a point near the posterior edge 315 of oral device 310. In this way, vacuum tube 320 ensures that negative pressure is applied along the posterior edge of oral device 310, a location closer to the soft palate. Vacuum tube 320 includes side holes 322 and an open distal end 324 through which negative pressure may be applied. Additionally, in this embodiment, tongue constraint 312 has no vacuum ports extending through plate 313 as in the earlier embodiment.

Another unique aspect of oral device 310 is the placement of spacing elements 324 on the inferior surface 326 of bite structure 311. Spacing elements 324 are a soft pliable material, e.g. polymeric tubing or foam, having a thickness of about 2-12 mm. Each spacing elements 324 is positioned at or near a posterior end 329 of bite structure 311 and extends anteriorly approximately 25-75% of the way around to the front of bite structure 311. Alternatively, multiple spacing elements of shorter length may be placed at intervals along each side of bite structure 31. In this way spacing elements 325 sit between the patient's upper and lower teeth and hold open the lower jaw slightly. Such slight opening of the jaw during sleep has been shown to improve airway patency in some circumstances.

A further unique aspect of oral device 310 is that a jaw positioning tab 328 is disposed on the anterior closed end of bite structure 311 and extends downwardly therefrom sufficiently to engage the posterior surface of the lower front teeth when oral device 310 is positioned in the oral cavity. Jaw positioning tab 328 is of sufficient stiffness and positioned in a suitable location on bite structure 311 to maintain the patient's lower jaw in a position slightly forward of a normal relaxed position. Such forward positioning of the jaw has been found to improve airway patency in some circumstances.

It should be understood that ribs 318, spacing element 324, and jaw positioning tab 328 are optional features of oral device 310 and that any or both of these features may be eliminated without departing from the scope of the invention or limiting its utility.

It will be understood that oral device 310 will usually include a lip seal. It should be further understood that any or all of the features of oral device 310 may optionally be included in oral device 10 or in other embodiments described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An oral device for temporary placement in a patient's oral cavity, the patient having a tongue and a jaw comprising a lower jaw and an upper jaw, said device comprising:
   an upper jaw brace;
   a lower jaw brace; and
   a tongue-engaging member coupled to at least one of the upper jaw brace and the lower jaw brace, said tongue-engaging member being disposed to engage a medial region of the tongue when the upper jaw brace is positioned on the upper jaw;
   wherein the upper jaw brace and the lower jaw brace are configured so that the lower jaw brace is advanced in an anterior direction relative to the upper jaw brace, and wherein the upper jaw brace includes a jaw positioning tab disposed to engage a posterior surface of lower teeth of the patient so as to maintain the lower jaw in a position forward of a normal relaxed position when the oral device is worn by the patient with the upper jaw in the upper jaw brace and the lower jaw in the lower jaw brace.

2. An oral device as in claim 1, further comprising a vacuum source which is connectable to the oral device.

3. An oral device as in claim 2, wherein the tongue-engaging member has an anterior surface and a posterior surface where the anterior surface is inclined forwardly relative to a plane of the patient's jaw and is disposed to engage a medial region of the tongue when the upper jaw brace is on the upper jaw.

4. An oral device as in claim 3, wherein the tongue-engaging member has an integral plenum connectable to the vacuum source with at least one port disposed on a posterior surface of the tongue-engaging member and open to the integral plenum.

5. An oral device as in claim 4, wherein the tongue-engaging member has a plurality of ports distributed over the posterior surface thereof.

6. An oral device as in claim 5, wherein the anterior surface and the posterior surface of the tongue-engaging member are inclined forwardly at an angle in a range from 45 degrees to 60 degrees relative to a plane of the upper jaw brace when positioned on the upper jaw.

7. An oral device as in claim 6, wherein the anterior surface of the tongue-engaging member is generally parallel to the posterior surface of the tongue-engaging member.

8. An oral device as in claim 2, wherein the vacuum source is adapted to draw a vacuum in a range from 1 $cmH_2O$ to 100 $cmH_2O$ through the oral device.

9. An oral device as in claim 2, wherein the tongue-engaging member has a vacuum port and a bleed port to allow a continuous air flow there through while maintaining a partial vacuum in the oral cavity.

10. An oral device as in claim 1, wherein the upper and lower jaw braces each comprise a U shaped bite plate configured to be positioned against a full dentition.

11. An oral device as in claim 1, wherein the upper jaw brace and the lower jaw brace are connected by a pair of rigid links, wherein each link is pivotally attached at one end to the upper brace and at another end to the lower brace to allow the braces to open and close.

12. An oral device as in claim 1, wherein the upper jaw brace and the lower jaw brace are connected by a pair of elastic bands which are secured over anchors formed on the braces.

13. An oral device as in claim 1, wherein the upper jaw brace and the lower jaw brace are fixedly attached to each other.

14. An oral device as in claim 1, wherein the lower jaw brace is advanced relative to the upper jaw brace by a distance in the range from 4 mm to 12 mm when the upper and lower jaw braces are closed together.

15. A method for maintaining an open airway in a patient having an oral cavity, a tongue, and a palate, said method comprising:
engaging a member against a medial region of the tongue to provide a clearance between the medial region and the palate; and
applying a vacuum within the oral cavity to draw together the soft palate and a posterior region of the tongue; and
advancing a lower jaw of the patient forward relative to an upper jaw while applying the vacuum,
wherein advancing the lower jaw relative to the upper jaw comprises capturing the upper jaw in an upper jaw brace and capturing the lower jaw in a lower jaw brace, wherein the braces are connected so that the lower jaw brace moves in an anterior direction relative to the upper jaw brace when the jaws are closed together,
wherein a jaw positioning tab on the upper jaw brace engages the lower jaw and forwardly advances the lower jaw beyond a normal relaxed position when the oral device is worn by the patient with the upper jaw in the upper jaw brace and the lower jaw in the lower jaw brace.

16. A method as in claim 15, wherein an anterior surface of the member is inclined forwardly relative to a plane defined between the patient's upper and lower teeth and the anterior surface engages the medial region of the tongue and displaces the medial region of the tongue in an anterior direction relative to the soft palate.

17. A method as in claim 16, wherein the vacuum in the oral cavity is applied to the clearance through ports disposed over a posterior surface of the member.

18. A method as in claim 16, wherein the lower jaw brace is advanced relative to the upper jaw brace by a distance in a range from 4 mm to 12 mm when the upper and lower jaw braces are closed together.

19. A method as in claim 15, wherein the upper jaw brace and the lower jaw brace are connected by a pair of rigid links, wherein each link is pivotally attached at one end to the upper brace and at another end to the lower brace to allow the braces to open and close.

20. A method as in claim 15, wherein the upper jaw brace and the lower jaw brace are connected by a pair of elastic bands which are secured over anchors formed on the braces.

21. A method as in claim 15, wherein the upper jaw brace and the lower jaw brace are fixedly attached to each other.

22. A method as in claim 15, wherein the vacuum in the oral cavity is in a range from 25 $cmH_2O$ to 50 $cmH_2O$.

23. A method as in claim 15, wherein applying the vacuum in the oral cavity comprises continuously drawing a vacuum while simultaneously bleeding in a controlled amount of air to maintain a desired partial vacuum.

24. A method as in claim 15, wherein the vacuum in the oral cavity draws the soft palate against the posterior surface of the member.

25. A method as in claim 15, wherein the soft palate remains spaced-apart from the posterior surface of the member while the vacuum in the oral cavity is being applied.

* * * * *